United States Patent [19]

van der Vies

[11] 4,071,623

[45] Jan. 31, 1978

[54] PHARMACEUTICAL PREPARATION ADAPTED FOR ORAL ADMINISTRATION

[75] Inventor: Johannes van der Vies, Oss, Netherlands

[73] Assignee: Akzona Incorporated, Asheville, N.C.

[21] Appl. No.: 687,267

[22] Filed: May 17, 1976

[30] Foreign Application Priority Data

May 30, 1975 Netherlands .......................... 7506407

[51] Int. Cl.² .......................... C07J 1/00; A61K 31/56
[52] U.S. Cl. ..................................... 424/238; 424/239; 260/397.5
[58] Field of Search ................ 260/397.5 A; 424/238, 424/239

[56] References Cited

U.S. PATENT DOCUMENTS

| | | | |
|---|---|---|---|
| 2,990,414 | 6/1961 | Ringold et al. | 260/397.5 |
| 3,519,659 | 7/1970 | Schmidlin et al. | 260/397.45 |
| 3,916,002 | 10/1975 | Taubert et al. | 260/397.5 |

OTHER PUBLICATIONS

Chem. Abstracts, vol. 77, (1972), Pars. 70535s.

*Primary Examiner*—Elbert L. Roberts
*Attorney, Agent, or Firm*—Robert H. Falk; Charles A. Wendel; Francis W. Young

[57] ABSTRACT

The invention relates to a novel pharmaceutical preparation with oestrogenic activity adapted for oral administration comprising an oestradiol-17$\beta$-ester, the ester group of which has been derived from aliphatic carboxylic acids having 9–16 carbon atoms, in combination with a non-steroidal lipoid. The preparation may additionally contain a progestational steroid or an androgen. The invention also relates to novel oestradiol-17$\beta$-esters.

32 Claims, No Drawings

PHARMACEUTICAL PREPARATION ADAPTED FOR ORAL ADMINISTRATION

The invention relates to a novel pharmaceutical preparation with oestrogenic activity adapted for oral administration, the said preparation containing a 17β-ester of oestradiol, and to methods for the preparation thereof. The invention also relates to novel 17β-esters of oestradiol.

Oestradiol and 17β-esters thereof are known. In medicine, these oestrogenic compounds are predominantly used for the treatment of women after ovarectomy, for climacteric complaints, for menstrual disorders and also after the menopause to prevent deprivation manifestations. In such cases, the oestrogens serve to compensate for a lack of endogenous oestrogen (substitution therapy). Oestrogens are further used in the treatment of certain types of inoperable mammary carcinoma in postmenopausal women and in the treatment of prostatic carcinoma of the man. The action of oestradiol-17β-esters is attributable to that of oestradiol, which is formed in the plasma by hydrolysis of the ester.

Oestradiol is administered parenterally, predominantly in the form of one of its 17β-esters. In this way a good effect is achieved with a relatively low dosage. Furthermore, the use of 17β-esters result in a depot effect, so that an effective oestrogen level in the plasma, persisting for several weeks, can be obtained with an intramuscular injection. By taking a mixture of 17β-esters with various absorption rates from the depot and/or different hydrolysis rates in the plasma, an oestrogen preparation with a prolonged action can be obtained, where the action commences very rapidly after the intramuscular administration and continues, for example, for several weeks.

There are also objections to the parenteral administration form. Patients are not capable of giving themselves an injection, and a doctor or medically trained personnel (a nurse) is therefore almost always necessary. Furthermore, repeated parenteral administration may cause local reactions. The parenteral administration of long-acting preparations is associated with a further disadvantage, in that the action thereof cannot be interrupted or stopped. An oral administration form would therefore be infinitely preferable to a parenteral form.

The above-noted effects of the parenteral administration form cannot however be achieved by administration of oestradiol or the 17β-esters thereof by the oral route when the same quantities of active substance are used; much larger quantities are necessary, sometimes 5-20 times as much.

The greatest part of the oestradiol or oestradiol-17β-ester given orally is rapidly inactivated by the liver and excreted as a metabolite. Only a fraction of the given dose is responsible for the final desired effect. It is obvious that on frequent administration in this way, the liver and other organs, such as kidneys, are taxed more, as a result of which undesired side-effects may appear.

It has been possible to substantially increase the effective activity on oral administration by introducing substituents into the oestradiol molecule. Known examples of such compounds are: ethinyl-oestradiol (17α-ethinyl-$\Delta^{1,3,5(10)}$-oestratrien-3,17β-diol), mestranol (3-methoxy-17α-ethinyl-$\Delta^{1,3,5(10)}$-oestratrien-17β-ol), quinestrenol (3-cyclopentyloxy-17α-ethinyl-$\Delta^{1,3,5(10)}$-oestratrien-17β-ol). The drawback of these synthesized oestradiol derivatives is that the activity profile usually differs from that of oestradiol, as a result of which, despite the advantages of the lower dosages, other associated effects, which are not always desired, particularly during long-term administration, have to be taken into account.

Surprisingly, it has now been found that the oral activity of oestradiol can be considerably improved if oestradiol is administered in the form of its 17β-esters derived from an aliphatic carboxylic acid with 9-16 carbon atoms and in the presence of a pharmaceutically acceptable non-steroidal lipoid. The lower and higher aliphatic carboxylic esters of oestradiol proved to have much less effect when given under these circumstances in the same dosages.

The invention therefore relates to a novel pharmaceutical preparation with oestrogenic properties adapted for oral administration, containing an ester of oestradiol, and is characterized by the incorporation into a pharmaceutical form suitable for oral administration of one or more oestradiol-17β-esters, derived from an aliphatic carboxylic acid with 9-16 carbon atoms, together with a pharmaceutically acceptable non-steroidal lipoid. The invention also encompasses the method for preparing said preparation.

The term "aliphatic carboxylic acid" also includes branched chain aliphatic and cycloaliphatic carboxylic acids.

In the preparation according to the invention, preferably one or more oestradiol esters derived from an aliphatic carboxylic acid with 10-14 carbon atoms are present. These esters have been shown to possess the highest activity, particularly the α- and β-methyl substituted aliphatic carboxylic acid esters.

As examples of aliphatic carboxylic acids with 9-16 carbon atoms, from which the oestradiol esters are derived, the following can be given: pelargonic acid, capric acid, undecanoic acid, lauric acid, tridecanoic acid, myristic acid, pentadecanoic acid, decenoic acid, undecenoic acid, palmitic acid and the branched-chain and cyclic analogues of these acids such as α-(and β-)methyl-caprylic acid, α-(and β-)methyl-pelargonic acid, α-(and β-)methyl-capric acid, β,β-dimethyl-pelargonic acid, β-(p-methyl-cyclohexyl)-propionic acid, β-(p-ethyl-cyclohexyl)propionic acid, β-(cycloheptyl)-propionic acid, α-(and β-)methyl-β-cyclohexyl propionic acid, cyclododecyl-carboxylic acid, adamantane carboxylic acid, adamantly-acetic acid and β-(bicyclo[2,2,2]octyl)propionic acid. The oestradiol ester is preferably derived from capric acid, undecanoic acid, lauric acid, tridecanoic acid, myristic acid or the α- or β-methyl-substituted or cyclic isomers of these acids.

Various of the oestradiol esters indicated above are novel compounds. The present invention therefore also comprises novel oestradiol esters with interesting oestrogenic properties, said novel oestradiol esters having the formula:

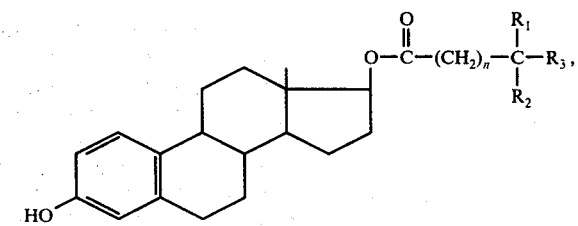

wherein, $n = 0$, 1 or 2, usually 0 or 1 and preferably 0; $R_1$ = alkyl (1–10 C), preferably $CH_3$; $R_2$ = H or alkyl (1–10 C), preferably H; $R_3$ = an aliphatic group having 1–18 C-atoms, preferably 6–12 C-atoms, which group may contain one or more rings having 5–12 C-atoms, preferably 5–7 C-atoms, or $R_1$ and $R_3$ form together with the C-atom to which they are attached a cycloaliphatic group having 7–12 C-atoms, or $R_1$, $R_2$ and $R_3$ form together with the C-atom to which they are attached a polycycloaliphatic group having 6–12 C-atoms, preferably 8–10 C-atoms, said cycloaliphatic or polycycloaliphatic group optionally being substituted by an aliphatic group having 1–6 C-atoms, with the proviso that the total number of C-atoms in the ester group is in the range of 8–20 C-atoms, preferably 9–16 C-atoms and still more preferably 10–14 C-atoms.

By pharmaceutically acceptable non-steroidal lipoids are meant plant and animal oils and fats consisting of the mono-, di- and triglycerides of various fatty acids or containing these as main constituents; fatty acid esters of alcohols; higher aliphatic alcohols; saturated and unsaturated fatty acids; the commercially available synthetic and semi-synthetic mono-, di-, and triglyceride oils and glycerol ethers; certain types of wax and mixtures of two or more of the above-noted substances. The lipoid substance is preferably liquid at normal temperature, that is, at a temperature in the range of about 10° C to about 30° C. The oestradiol ester is then dissolved in the lipoid substance and the solution is incorporated into a preparation or, as the case may be, converted into a pharmaceutical form. At normal temperature a part of the ester may be present in the liquid lipoid as a suspension, in which case the quantities of ester and lipoid substance are mutually adjusted in such a way that at body temperature the ester is completely dissolved in the lipoid substance. The intensification of the oral activity of the oestradiol esters according to the invention appears to be the greatest when a lipoid substance liquid at normal temperature is used.

Examples of lipoid substances which may be used in the preparation according to the invention are: arachis oil, castor oil, sesame oil, linseed oil, soya bean oil, sunflower seed oil, olive oil, fish liver oil, ethyl oleate, oleyl oleate, glyceryl trioleate, glyceryl dioleate, glyceryl monooleate, cetyl alcohol, stearyl alcohol, capric acid, undecenoic acid, undecanoic acid, lauric acid, oleic acid, synthetic glycerides of saturated fatty acids, with 8 to 10 or 12 carbon atoms such as the commercial products Syndermin GTC and Miglyol 812, polyoxyethylene derivatives of glycerol such as the commercial product Labrafil 1944, bee's wax and mixtures of two or more of these substances.

The invention provides an oral pharmaceutical preparation with oestrogenic activity. The invention also offers the possibility of providing an orally active pharmaceutical preparation, which in addition to oestrogenic properties also possesses androgenic or gestagenic properties, by incorporating an orally active androgen or gestagen in the preparation.

Orally active pharmaceutical preparations with both oestrogenic and androgenic activity are known. Such a preparation usually contains an orally active oestrogen, such as 17α-ethinyl-oestradiol or mestranol, as the oestrogenic component, and an orally active androgen, such as 17α-methyl-testosterone, as the androgenic component, the two components being present in a certain ratio. Conditions in which such preparations are used include climactic complaints, for improvement of sleep and the feeling of wellbeing in older women, in cases of frigidity, hypogonadism, peripheral vascular disorders, oesteoporosis and after castration. Such a preparation has a positive influence on protein and calcium metabolism; and may reduce or even rectify a disorder of the hormonal balance in the climacteric or after castration. When used in cases of frigidity, the androgenic component increases the libido and the oestrogenic component contributes to the recovery of a possibly atrophic mucosa. In oesteoporosis, the oestrogenic component brings about a decrease in oesteoclastic activity and the androgenic component stimulates the building up of the bone matrix.

As an orally active androgen for incorporation in the oestrogen preparation according to the invention, preference is given to one or more testosterone esters and/or 5α-dihydrotestosterone esters, derived from an aliphatic carboxylic acid with 9–16 carbon atoms, preferably 10–12 carbon atoms. The preparation of orally active formulations with androgenic activity on the basis of the named testosterone and/or 5α-dihydrotestosterone esters forms the subject of the copending, not previously published Dutch Patent application No. 74.02689.

The androgen ester may be derived from the same aliphatic carboxylic acid as the oestradiol ester and is preferably derived from capric acid, undecanoic acid or lauric acid.

The presence of the oily component in the preparation according to the present invention also results in intensification of the oral androgenic activity of the testosterone and/or 5α-dihydrotestosterone esters. In this way, an oral preparation possessing both oestrogenic and androgenic activity is obtained, which furthermore possesses the advantage that the action of the preparation is based on that of natural hormones, which are formed in the body by hydrolysis of the esters.

Orally active pharmaceutical preparations with both oestrogenic and gestagenic activity are also known. This combination is mainly known from oral contraceptives of the so-called combination type, in which an orally active gestagenic substance, such as chlormadinone acetate, lynestrenol, norethisterone, norethynodrel or norgestrel, has been combined with an orally active oestrogenic substance, such as ethinyl-oestradiol or mestranol. In such preparations, the oestrogen component can be replaced by one or more oestradiol esters, derived from an aliphatic carboxylic acid with 9–16 C-atoms, together with a lipoid substance according to the invention. With respect to the combination of an oestrogen with a gestagen, within the context of the present invention, thought is however primarily directed at combination preparations which find use during and after the menopause, after castration and in hypogonadism, and where attempts are made to produce restitution of the hormonal balance to such an extent that in addition to other positive effects on body functions, osteoporosis in particular is checked. (See in this connexion, for example, the article by J. C. Gallagher and B. E. C. Nordin in "The Hormone", Volume XXXVII, pages 59–73 (1973) entitled: "Hormones and calcium metabolism"). For the preparation of formulations which can be used for such an indication, an orally active gestagenic agent is appropriately also incorporated into the preparation according to the invention, for example, norethisterone, lynestrenol or ethynodiol diacetate.

The preparation according to the invention can be administered orally in various dosage forms, for example in the form of tablets, capsules, grains, pills, boli, dragees, powders, granulates or microcapsules. In addition to the oestrogen ester(s), the lipoid substance and optionally the androgenic or gestagenic compound, the dosage form may contain one or more of the usual excipients, for example benzyl alcohol to increase the solubility of the active substance in the oil component, water, thickening agents such as gelatin or agar, polyethylene glycols, lactose, starch, talc or magnesium stearate. Other agents, such as preservatives, emulsifying agents, stabilizing agents, wetting agents, flavours, dyes, fillers, binding agents and/or encapsulating agents may optionally also be present.

The capsules may be soft or hard gelatin capsules, in which the active principle and the lipoid may be present in granular or finely divided intimate admixture or may be present in the form of an oily solution or suspension.

The combination of oestradiol-17β-ester and lipoid, when liquid or semi-liquid, may also be processed to solid oral formulations such as pills or tablets. For that purpose the oily solution of oestradiol-17β-ester is, for example, absorbed on calcium phosphate, lactose or cellulose derivatives and then processed to tablets or pills in the usual way. Combinations of oestradiol-17β-esters with lipoids, such as glycerylmono-oleate or capric acid, which are solid or semi-solid at room temperature, but are liquid at body temperature, may be granulated and processed to coated pills or tablets.

As already noted above, the oestradiol esters according to the invention are preferably administered dissolved in lipoid substances liquid at normal temperature, such as, for example, vegetable and animals oils, oleic acid, linoleic acid or undecenoic acid. When the androgenic or gestagenic component is present, this is preferably also dissolved in the oil, in addition to the oestradiol ester.

The most suitable oral administration form for this liquid form of the preparation according to the invention is the soft gelatine capsule or microcapsule. In accordance with a method usual in the techniques, the oily solution containing the active components and optionally other ingredients is encapsulated to soft gelatine capsules or microcapsules and the desired dimensions and containing the desired amount(s) of active substances. The microcapsules can also be processed to tablets or pills according to the well-known pharmaceutical formulation methods.

The oestradiol-17β-ester(s) concentration in the preparation according to the invention can vary within considerable limits, on the understanding that the amount of oestradiol-17β-ester(s) by weight does not exceed the amount of lipoid substance by weight or in other words the oestradiol-17β-esters(s) concentration in the preparation is 50% by weight or less and is usually in the range of 0.01-10% by weight.

As indicated above, the amount of lipoid by weight in the preparation according to the invention is equal to or higher than the amount of oestradiol-17β-ester by weight. Depending on the other constituents present in the preparation (excipients, capsule shell, coating) the amount of lipoid substance per dosage unit will vary from 25 to 95% by weight and is usually in the range of 50-80% by weight. The amount of oestradiol-17β-ester(s) per dosage unit, for example a capsule or a tablet, may also vary within wide limits, for example from 0.001 mg to 2 mg, and is preferably between 0.005 mg and 1 mg.

When the androgen ester is present in the preparation according to the invention, the amount thereof per dosage unit is within the range 0.5 to 400 mg, and the requirement, that the amount of androgen ester by weight does not exceed the amount of lipoid substance by weight, also applies. When the gestagenic substance is present in the preparation according to the invention, the amount thereof per dosage unit is within the range 0.1 to 20 mg, and is preferably between 0.2 and 10 mg.

The exceptional oestrogenic properties of the preparations according to the invention have been demonstrated using the known Allen-Doisy test (J.A.M.A. (1923), 81, pages 819-821) in castrated female rats. The oestradiol-17β-esters were administered orally, dissolved in arachis oil. The results are given in table A.

Table A

| Oestradiol-17β-ester | Dosage | | |
|---|---|---|---|
| | 8 µg | 16 µg | 32 µg |
| -formate | 0/8 | 0/8 | 1/8 |
| -pentanoate | 0/8 | 0/8 | 0/8 |
| -octanoate | 0/8 | 1/8 | 2/8 |
| -decanoate | 2/8 | 6/8 | 7/8 |
| -α-methyl-decanoate | 8/8 | 8/8 | 8/8 |
| -β-methyl-decanoate | 6/8 | 8/8 | 8/8 |
| -undecanoate | 2/8 | 7/8 | 8/8 |
| -dodecanoate | 2/8 | 6/8 | 7/8 |
| -tetradecanoate | 1/8 | 6/8 | 6/8 |
| -hexadecanoate | 0/8 | 0/8 | 6/8 |
| -octadecanoate | 0/8 | 0/8 | 2/8 |

Studies with other lipoid substances, such as sesame oil, soya bean oil, glyceryl trioleate, oleic acid and undecanoic acid gave similar results. It appears obvious that oestradiol-17β-esters derived from carboxylic acids with 9-16 C-atoms are much more active than the other esters and that in particular the esters with 10-14 carbon atoms in the ester group are very active.

Clinical trials in ovariectomized and in menopausal women, given a daily dosage of 0.1-0.5 mg oestradiol-17β-ester, administered in an oral preparation according to the invention, revealed favourable oestrogenic effects, which suggest the potency of the preparation in EDS-therapy.

During clinical trials in post-menopausal women, given a daily dosage of 1-3 dosage units of an oestrogen and of an oestrogen-gestagen preparation according to the invention for 6 weeks, a distinct decrease in the plasma calcium level was noted, which suggests an antiosteoporotic effect.

The invention is further illustrated by means of the following examples.

EXAMPLE I

Soft Gelatine Capsules

A sterile solution of oestradiol-17β-decanoate in arachis oil, containing 4.167 g per liter, was prepared. This solution was encapsulated in soft gelatine capsules with due regard for aseptic precautions. The soft gelatine capsules obtained had a content of 0.12 ml, so that the amount of active agent present was 0.5 mg per capsule. The capsule wall consisted of 70% gelatine, 16% glycerol, 12% sorbitol, 0.4% of the sodium salts of ethyl/propyl-p-hydroxybenzoate, 0.5% $TiO_2$ and 1.1% Cochineal Red (dye).

In a similar way, a number of oestradiol-17β-esters in various lipoid substances were processed to give soft gelatine capsules, details of which are given in table B.

Table B

| -17β-ester | lipoid substance | content of capsule | mg active substance/capsule |
| --- | --- | --- | --- |
| -decanoate | oleic acid | 0.12 | 0.25 |
| α-methyl-decanoate | sesame oil | 0.08 | 0.1 |
| β-methyl-decanoate | undecenoic acid | 0.18 | 0.2 |
| -undecanoate | soya bean oil | 0.12 | 0.2 |
| -dodecanoate | ethyl oleate | 0.12 | 0.25 |
| -tetradecanoate | linseed oil | 0.18 | 0.5 |
| α-methyl-β-cyclohexyl-propionate | arachis oil | 0.18 | 0.5 |
| cyclododecanyl-carboxylate | oleic acid | 0.12 | 0.5 |

EXAMPLE II

Tablets

Example II

| Tablets | |
| --- | --- |
| Oestradiol-17β-decanoate | 0.5 mg |
| Capric acid | 82.5 mg |
| Lactose | 145.0 mg |
| Potato starch | 20.0 mg |
| Magnesium stearate | 1.5 mg |
| Citric acid | 0.5 mg |
| | 250.0 mg |

Oestradiol-17β-undecanoate was dissolved with gentle warming in capric acid, after which the solution was homogeneously absorbed in the lactose. After mixing with potato starch, citric acid and a little water, the thus-obtained granulate was dried. The dry granulate was mixed with the magnesium stearate and tabletted in the usual way.

Tablets with the following composition were prepared in a similar way:

| oestradiol-17β-undecanoate | 0.5 mg |
| --- | --- |
| testosterone undecanoate | 40.0 mg |
| glyceryl mono-oleate | 150.0 mg |
| lactose | 48.0 mg |
| methyl cellulose | 20.0 mg |
| magnesium stearate | 1.5 mg |
| | 250.0 mg |
| Oestradiol-17β-α'-methyl-decanoate | 0.5 mg |
| Lynestrenol | 2.5 mg |
| Bee's wax/stearyl alcohol | 100.0 mg |
| Lactose | 118.0 mg |
| Methyl cellulose | 28.0 mg |
| Magnesium stearate | 1.0 mg |
| | 250.0 mg |

EXAMPLE III

Hard Gelatine Capsules

Example III

| Hard gelatine capsules | |
| --- | --- |
| Oestradiol-17β-dodecanoate | 0.25 mg |
| Chlormadinon acetate | 4.00 mg |
| Lauric acid | 95.75 mg |
| | 100.0 mg |

Oestradiol-17β-dodecanoate and chlormadinon acetate are dissolved in lauric acid at 50° C. After cooling, the solid mixture is powdered, and hard gelatine capsules are filled with the finely-divided mixture (100 mg mixture per capsule).

EXAMPLE IV

Soft Gelatine Capsules

Soft gelatine capsules with contents as indicated below were prepared in a way similar to that described in example I.

| a) Oestradiol-17β-decanoate | 0.02 mg |
| --- | --- |
| Testosterone-17β-decanoate | 10.00 mg |
| Oleic acid to | 0.18 ml |
| b) Oestradiol-17β-undecanoate | 0.1 mg |
| Norethisterone | 2.0 mg |
| Arachis oil to | 0.12 ml |

EXAMPLE V

Preparation of Novel Esters

To a solution of 2 g oestradiol in a mixture of 8 ml pyridine and 8 ml acetone, cooled to −10° C, was added dropwise a solution of 4 ml α-methyl-β-cyclohexyl-propionylchloride in 12 ml acetone. The mixture was stirred for 16 hours at 0° C and 6 hours at room temperature. After cooling to −10° C a solution of 1 ml α-methyl-β-cyclohexylpropionylchloride in 5 ml acetone was added and the mixture was stirred for 16 hours at room temperature. The reaction mixture was poured out in ice-water (8 g) and stirred for some time to decompose excess acid chloride. The mixture was extracted with methylenechloride. The extract (4 g) containing oestradiol 3,17β-diester, was evaporated to dryness and the residue was dissolved in a mixture of methanol (19 ml) and tetrahydrofuran (19 ml). The solution was cooled, whereafter a solution of 350 mg potassiumhydroxide in a mixture of 4.8 ml methanol and 2 ml tetrahydrofuran was added. Stirring was effected for 4 hours, while gradually increasing the temperature of 0° C. The reaction mixture was poured out in ice-water. Extraction with methylene-chloride, chromatography on silicagel with toluene/ethylacetae 95/5 and crystallization from ether gave 1.5 g oestradiol-17β-(α-methyl-β-cyclohexyl-propionate), m.p. 154°–156° C; $[\alpha]_D^{20} = +39°$ (in $CH_2Cl_2$).

In a similar manner the following 17β-esters of oestradiol were prepared:
α-methyl-decanoate,
β-methyl-decanoate,
α,α-dimethyl-decanoate,
β-cyclohexyl-butyrate,
cyclodecanoylcarboxylate,
β-propyl-hexanoate,
γ,γ-diethyl-hexanoate,
α-octyl-dodecanoate,
adamantane-1'-carboxylate,
α,α-dimethyl-octadecanoate,
α-ethyl-heptanoate, cycloheptylcarboxylate,
cyclo-octylacetate,
α,α-dimethyl-heptanoate,
α-methyl-hexadecanoate,
α-ethyl-tetradecanoate.

I claim:

1. A pharmaceutical preparation with oestrogenic activity adapted for oral administration comprising an oestrogenically effective amount when orally administered of at least one 17β-ester of oestradiol having the formula

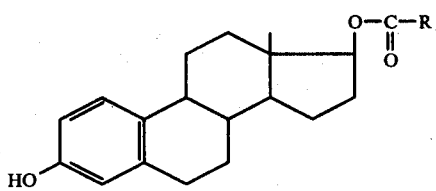

the ester group thereof being derived from an aliphatic carboxylic acid having 9 to 16 carbon atoms, and
a pharmaceutically acceptable non-steroid lipoid carrier, wherein said 17-β ester of oestradiol constitutes from 0.01 to 50% by weight of said preparation and said non-steroid lipoid carrier is present in an amount of at least equal to the amount of said 17β-ester of oestradiol.

2. Preparation according to claim 1 wherein said ester has been derived from an aliphatic carboxylic acid having 10-14 carbon atoms.

3. Preparation according to claim 1 wherein said lipoid is liquid at ambient temperarure.

4. Preparation according to claim 1 which comprises as an additional active ingredient an orally active androgen or gestagen.

5. Preparation according to claim 4 wherein said orally active androgen is an ester selected from the group consisting of esters of testosterone and 5α-dihydrotestosterone, the ester group of which has been derived from an aliphatic carboxylic acid having 9-16 carbon atoms.

6. Preparation according to claim 1 wherein said ester of oestradiol constitutes 0.01-10% by weight, of said preparation.

7. Preparation according to claim 1, wherein said lipoid constitutes 25-95% by weight of said preparation, preferably 50-80% by weight.

8. Preparation according to claim 1 in unit dosage form comprising from 0.001 to 2 mg of said ester of oestradiol.

9. Preparation according to claim 1 in unit dosage form consisting of a soft gelatine capsule containing a solution of said oestradiol ester in said lipoid.

10. A process for conducting estrogen deficiency therapy in a female patient requiring such therapy comprising orally administering daily to said patient from 0.001 to 2 mg of the oestradiol-ester preparation of claim 1 together with a non-steroidal lipoid, the amount of said lipoid being equal to or higher than the amount of said ester or esters.

11. A 17β-ester of oestradiol having the formula:

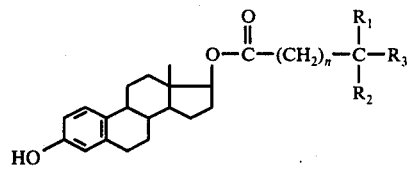

wherein
n = 0, 1 or 2;
$R_1$ = alkyl having 1-10 carbon atoms;
$R_2$ = H or alkyl having 1-10 carbon atoms;
$R_3$ = an aliphatic group having 1-18 carbon atoms, which group may contain a ring having 5-12 carbon atoms;
or $R_1$ and $R_3$ form together with the carbon atom to which they are attached and a cycloaliphatic group having 7-12 carbon atoms, said cycloaliphatic group optionally being substituted by an aliphatic group having 1-6 carbon atoms, with the proviso that the total number of carbon atoms in the ester group is in the range of 8-20 carbon atoms.

12. A compound according to claim 11, wherein n = 0 and $R_2$ = H.

13. A compound according to claim 11, wherein n = 1 and $R_2$ = H.

14. A compound according to claim 12, wherein $R_1$ = methyl.

15. A compound according to claim 13, wherein $R_1$ = methyl.

16. A compound according to claim 12, wherein $R_1$ and $R_3$ form together with the carbon atom to which they are attached a cycloaliphatic group having 7-12 carbon atoms.

17. A compound according to claim 13, wherein $R_1$ and $R_3$ form together with the carbon atom to which they are attached a cycloaliphatic group having 7-12 carbon atoms.

18. Preparation according to claim 1 in unit dosage form comprising from 0.005 to 1 mg of said ester of oestradiol.

19. The pharmaceutical preparation of claim 1 wherein said 17β-ester of oestradiol is oestradiol-17β-decanoate.

20. The pharmaceutical preparation of claim 1 wherein said 17βester of oestradiol is oestradiol-17α'-methyl decanoate.

21. The pharmaceutical preparation of claim 1 wherein said 17β-ester of oestradiol is oestradiol-17β-β'-methyl decanoate.

22. The pharmaceutical preparation of claim 1 wherein said 17β-ester of oestradiol is oestradiol-17β-undecanoate.

23. The pharmaceutical preparation of claim 1 wherein said 17β-ester of oestradiol is oestradiol-17β-dodecanoate.

24. The pharmaceutical preparation of claim 1 wherein said 17β-ester of oestradiol is oestradiol-17β-tetradecanoate.

25. The pharmaceutical preparation of claim 1 wherein said 17β-ester of oestradiol is oestradiol-17β-α'-methyl-β'-cyclohexyl-propionate.

26. The compound of claim 11 which is oestradiol-17β-α'-methyl decanoate.

27. The compound of claim 11 which is oestradiol-17β-β'-methyl decanoate.

28. The compound of claim 11 which is oestradiol-17β-α'-methyl-β'-cyclohexyl propionate.

29. The compound of claim 11 which is oestradiol-17β-β'-cyclohexyl butyrate.

30. The compound of claim 11 which is oestradiol-17β-cyclo-octyl acetage.

31. The compound of claim 11 which is oestradiol-17β-α'-ethyl hexanoate.

32. The compound of claim 11 which is oestradion-17β-α'-propylpentanoate.

* * * * *